United States Patent
Atsumi et al.

(10) Patent No.: US 7,968,322 B2
(45) Date of Patent: Jun. 28, 2011

(54) HYDROGEN FERMENTOR AND METHOD OF PRODUCING HYDROGEN

(75) Inventors: Ryo Atsumi, Shibuya-ku (JP); Yasuhiro Oki, Yaizu (JP); Taiju Masuda, Yaizu (JP); Yutaka Mitani, Yaizu (JP)

(73) Assignee: Sapporo Breweries Limited, Tokyo (JP)

(*) Notice: Subject to any disclaimer, the term of this patent is extended or adjusted under 35 U.S.C. 154(b) by 468 days.

(21) Appl. No.: 12/090,734

(22) PCT Filed: Oct. 6, 2006

(86) PCT No.: PCT/JP2006/320084
§ 371 (c)(1),
(2), (4) Date: Apr. 18, 2008

(87) PCT Pub. No.: WO2007/060791
PCT Pub. Date: May 31, 2007

(65) Prior Publication Data
US 2009/0263876 A1    Oct. 22, 2009

(30) Foreign Application Priority Data
Nov. 22, 2005    (JP) ................ 2005-337666

(51) Int. Cl.
*C12P 3/00*    (2006.01)
*C12M 1/02*    (2006.01)

(52) U.S. Cl. ................ 435/168; 435/289.1

(58) Field of Classification Search .......... None
See application file for complete search history.

(56) References Cited

FOREIGN PATENT DOCUMENTS

| | | |
|---|---|---|
| JP | 2001 149983 | 6/2001 |
| JP | 2002 272491 | 9/2002 |
| JP | 2003 251312 | 9/2003 |
| JP | 2004 41929 | 2/2004 |
| JP | 2005 13045 | 1/2005 |
| JP | 2005 66420 | 3/2005 |
| JP | 2005 125149 | 5/2005 |
| JP | 2005 193122 | 7/2005 |
| JP | 2005 224777 | 8/2005 |

OTHER PUBLICATIONS

Oki, Yasuhiro, et al. "A Study of Hydrogen Production From Food Factory Wastes by Anaerobic Fermentation", Proceedings of the 59th Annual Meeting of the Society for Biotechnology, Japan, 2007, (with English translation).

*Primary Examiner* — Herbert J. Lilling
(74) *Attorney, Agent, or Firm* — Oblon, Spivak, McClelland, Maier & Neustadt, L.L.P.

(57) ABSTRACT

The hydrogen fermentation apparatus is the one that generates hydrogen by decomposing organic matter through hydrogen fermentation. There are arranged a hydrogen fermentor which holds the treating liquid containing organic matter, and a string-shape carrier which is positioned to immerse itself in the treating liquid in the hydrogen fermentor, and on which hydrogen-generating bacteria are fixed.

8 Claims, 7 Drawing Sheets

HYDROGEN FERMENTOR AND METHOD OF PRODUCING HYDROGEN

TECHNICAL FIELD

The present invention relates to a hydrogen fermentation apparatus which generates hydrogen from organic matter through hydrogen fermentation, and to a production method of hydrogen.

BACKGROUND ART

Conventionally, disposal of food waste such as garbage and of agricultural and livestock waste has become a serious social issue. To this point, the development of biomass treatment technology is wanted.

Responding to the movement, there is promoted the development of technology to treat organic waste using anaerobic fermentation. Conventional anaerobic fermentation is governed by the one aiming at the methane formation through the decomposition of organic matter. That type of anaerobic fermentation consists of two steps: the acid-forming step which conducts hydrolysis of organic matter such as carbohydrate, protein, and lipid to generate organic acid; and the methane fermentation step which decomposes the organic acid into methane, carbon dioxide, and water, (for example, refer to Patent Documents 1 to 3.)

The above acid-forming step is also called a hydrogen fermentation step because hydrogen is generated on decomposing the organic matter. The conventional anaerobic fermentation did not focus on the hydrogen, and the generated hydrogen has been consumed for use by the methane bacillus, reduction of electron acceptor and acquisition of energy by other bacteria, and so on.

In recent years, the hydrogen fermentation aiming at the hydrogen-generation through the decomposition of organic matter has drawn attention from the viewpoint of effective use of hydrogen as a clean energy, (for example, refer to Patent Documents 4 to 6.).

Patent Document 1: JP-A-2001-149983 (the term "JP-A" referred to herein signifies the "Unexamined Japanese Patent Publication.)
Patent Document 2: JP-A-2005-66420
Patent Document 3: JP-A-2005-125149
Patent Document 4: JP-A-2003-251312
Patent Document 5: JP-A-2005-13045
Patent Document 6: JP-A-2005-193122

DISCLOSURE OF THE INVENTION

Problems to be Solved by the Invention

Above Patent Documents 1 to 6 adopt the complete mixing type of the biological treatment tank which operates in a state of suspended microorganisms in the treating liquid. In the field of biological treatment, however, there is a widely known technology of fixing microorganisms on a carrier aiming to increase the concentration of microorganisms in the tank to improve the rate of removing pollutants. That kind of treatment method using a carrier has several types: the fixed bed method which conducts treatment by fixing a carrier, on which microorganisms are fixed, at a specified position in the tank; and the fluidized bed method which makes a carrier, on which microorganisms are fixed, fluidize by supplying the carrier in the tank.

Any of above fixed bed method and fluidized bed method, however, has problems described below when they are applied to the hydrogen fermentation, and has to be improved before practical application.

That is, for the case of fixed bed method, the carrier is fixed so that the heterogenesis of microorganisms is difficult to proceed, and dead bacteria remain on the surface of the carrier to decrease the contact area between organic matter and carrier, which decreases the treatment efficiency. Further, when the treating liquid for hydrogen fermentation contains solid matter, unnecessary solid matter adheres to the surface of carrier or plugs, clogs, or jams the carrier, which also decreases the treatment efficiency. As a result, maintenance such as backwashing is required.

On the other hand, for the case of fluidized bed method, the carriers contact with each other during fluidization of carrier to separate microorganisms from the carrier to an adequate degree, thus suppressing the decrease in the contact area between the treating liquid and the carrier. Therefore, the fluidized bed method may be suitable in terms of treatment efficiency compared with the fixed bed method. According to a study of the inventors of the present invention, however, the fluidized bed method does not easily sustain the homogeneous fluidization against the variations of concentration of solid matter and the variations of property and specific gravity of treating liquid, and the sufficient treatment efficiency is not necessarily attained easily. In particular, when the treating liquid contains a large quantity of solid matter, the contact between the carrier suspending in the treating liquid and the solid matter sedimented to the lower section of the treating liquid becomes difficult, which decreases the treatment efficiency of hydrogen fermentation. Furthermore, the separation of the fluidized carrier from the treating liquid is difficult, and when the treating liquid contains solid matter, the hydrogen-generating bacteria adhere to the solid matter to likely induce the flow out of the hydrogen-generating bacteria from the hydrogen fermentor.

The present invention has been made to solve the above problems of related art, and an object of the present invention is to provide a hydrogen fermentation apparatus which, on generating hydrogen from organic matter through hydrogen fermentation, assures efficient and stable treatment of treating liquid even when the treating liquid contains solid matter, and fully suppresses the flow out of the hydrogen-generating bacteria from the hydrogen fermentor, and to provide a method for manufacturing hydrogen.

Means to Solve the Problems

To solve the above problems, the present invention provides a hydrogen fermentation apparatus for generating hydrogen by decomposing organic matter through hydrogen fermentation, comprising: a hydrogen fermentor accommodating a treating liquid containing organic matter; and a string-shape carrier, on which hydrogen-generating bacteria are fixed, being located in the hydrogen fermentor so as to contact with the treating liquid.

The term "hydrogen-generating bacteria" referred to herein signifies the microorganisms which have an ability to generate hydrogen.

According to the hydrogen fermentation apparatus of the present invention, a string-shape carrier is used as the carrier to fix the hydrogen-generating bacteria. Consequently, the hydrogen-generating bacteria and the organic matter in the treating liquid are sufficiently and stably held on the carrier, and the contact efficiency between them is increased. As a result, the hydrogen fermentation by the hydrogen-generating bacteria is effectively conducted. Since the string-shape carrier is flexible in nature, it efficiently and surely conducts the separation of unnecessary solid matter, dead hydrogen-generating bacteria, and the like adhered to the string-shape carrier, and further conducts the separation of hydrogen gas generated deep in the fibers of string-shape carrier owing to the treating liquid flow created by the entering and exiting flow of treating liquid to and from the tank and further by the flow of treating liquid induced by agitation and circulation thereof during the hydrogen fermentation treatment.

If the treating liquid contains a large quantity of solid matter, for example 250 mg/L or more of solid matter concentration in the treating liquid, conventional hydrogen fermentation apparatus fails to satisfy the necessary quantity of generated hydrogen and the reduction rate of solid matter. With the hydrogen fermentation apparatus according to the present invention, however, sufficient volume of hydrogen can be generated, and the quantity of solid matter in the treating liquid can fully be decreased.

Furthermore, since the hydrogen fermentation apparatus according to the present invention fixes the hydrogen-generating bacteria on the string-shape carrier, there is no need of means for separating the carrier from the treating liquid, which separation means is required in the fluidized bed method of related art, and the flow out of the hydrogen-generating bacteria from the hydrogen fermentor can sufficiently be suppressed.

Accordingly, the hydrogen fermentation apparatus of the present invention performs excellent contact between the treating liquid and the hydrogen-generating bacteria which are fixed on the string-shape carrier, conducts efficiently and stably the hydrogen fermentation, and fully suppresses the flow out of the hydrogen-generating bacteria from the hydrogen fermentor even when the treating liquid contains solid matter.

The above-described effects of the hydrogen fermentation apparatus according to the present invention are attained on the basis of the findings of the inventors of the present invention: sufficient and stable contact between the hydrogen-generating bacteria and the organic matter is critical for the case of relatively slow hydrogen fermentation, while the hydrogen fermentation apparatus in the related art is insufficient to this point. The effects of the present invention are that the hydrogen-generating bacteria and the organic matter can be sufficiently and stably held on the carrier by applying the treating method that uses a string-shape carrier, which is classified to the fixed bed method, to the hydrogen fermentation, and further that the adhered substances and the hydrogen gas generated in the course of progress of hydrogen fermentation can be efficiently separated from the fixing carrier. These effects are unexpected in view of the technological level of the related art that the fluidized bed method is accepted as suitable for the hydrogen fermentation in terms of treatment efficiency. The term "fixed bed", (also referred to as "fixed layer"), referred to herein signifies the structure of reaction layer, in which, when a fluid is introduced to a reactor containing particles and the like, the particles are not moving at a low flow rate of fluid, while the fluid passes through the gap between particles, (refer to "Bioreactor", Atokinson, translated by Saburo Fukui and Tsuneo Yamane as "Tubular Fermentor"). The term "fluidized bed", (also referred to as "fluidized layer"), referred to herein signifies the structure of reactor in which, when a fluid is introduced to a reactor containing particles and the like and when the charge rate of the fluid is increased, the flow resistance applied to the particles becomes equal to the weight of the particles at a certain flow velocity, and in the flow region above the equal velocity, the particles become to a dynamically suspended state. Thus, the particle layer expands in the reactor, and they move without staying at a point. Also the total particle layer likely becomes a flowing condition to resemble a single fluid layer. That type of particle layer condition is called the fluidized bed or the fluidized layer, (refer to "Fluidized bed and Spouted bed" of Chemical Engineering Handbook, edited by The Society of Chemical Engineers, Japan.)

The string-shape carrier in the hydrogen fermentation apparatus according to the present invention preferably has a braid structure in which a plurality of small loops of fibers form a lace-like pattern. With the use of that string-shape carrier having such a braid structure, a large quantity of hydrogen-generating bacteria can be fixed on the string-shape carrier, and the holdability of organic matter on the string-shape carrier and the separability of adhered substances and hydrogen gas from the string-shape carrier can be improved.

The hydrogen fermentation apparatus according to the present invention preferably further comprises a holder holding the string-shape carrier in a stretching state by fixing both ends of the string-shape carrier. With the holder, a desired positioning of the string-shape carrier is attained while fully assuring the holdability of the organic matter on the string-shape carrier, thus increasing the freedom of the apparatus design. In addition, when the hydrogen fermentation apparatus has a plurality of string-shape carriers, the interwinding phenomenon of the string-shape carriers under a generated flow of treating liquid is prevented. The string-shape carrier may be fixed only at one end thereof. In that case, however, interwinding of string-shape carriers and further the rubbing of string-shape carriers with each other likely occur. Consequently, for the hydrogen fermentation which is a relatively mild fermentation, the holdability of the organic matter on the string-shape carrier is deteriorated, and the treatment efficiency may decrease.

The holder preferably comprises two end faces which are positioned to face with each other and have a network structure, and a frame which holds the two end faces at a specified distance therebetween, while the string-shape carrier is fixed at both ends thereof to the respective two end faces of the holder. With the configuration, the treating liquid passes through the mesh opening at the end face of the holder even when a flow of treating liquid occurred along the stretching direction of the string-shape carrier, thus the reduction of contact efficiency between the hydrogen-generating bacteria fixed on the string-shape carrier and the organic matter is fully suppressed.

The hydrogen fermentation apparatus according to the present invention preferably further comprises a mixing means mixing the treating liquid in the hydrogen fermentor, and the mixing means preferably has a stirrer which is capable of rotating around a rotary shaft extending in the stretching direction of the string-shape carrier. With that mixing means to agitate the treating liquid in the hydrogen fermentor, the flow of treating liquid reaches deep into the fibers of the string-shape carrier, which further improves both the holdability of organic matter on the fixing carrier and the separability of adhered substances and hydrogen gas from the fixing carrier, thus achieving extremely high level of treatment efficiency.

The mixing means of the hydrogen fermentation apparatus according to the present invention preferably has a circulation line connected to the hydrogen fermentor at both ends thereof and creates a flow of the treating liquid within the hydrogen fermentor by withdrawing the treating liquid in the hydrogen fermentor from one end thereof and introducing the treating liquid into the hydrogen fermentor from the other end thereof.

With that circulation line to circulate the treating liquid in the hydrogen fermentor, extremely high level of treatment efficiency is attained. In this case, the stirrer may be existed or not existed. Even if the stirrer is not existed, the circulation line effectively functions as a mixing means. Therefore, scale up of the hydrogen fermentation apparatus is readily performed. Furthermore, mixing means with the circulation line and without stirrer has no influence of sheering force caused by the stirrer. Accordingly, even when the hydrogen-generating bacteria which are easily affected in their growth by shearing force are used, the hydrogen fermentation is favorably realized.

In addition, the present invention provides a method for manufacturing hydrogen by decomposing organic matter through hydrogen fermentation, comprising the step of bringing the treating liquid containing organic matter into contact, within the hydrogen fermentor, with the string-shape carrier on which hydrogen-generating bacteria are fixed.

According to the method for manufacturing hydrogen of the present invention, use of a string-shape carrier as the carrier to fix hydrogen-generating bacteria can sufficiently and stably hold the hydrogen-generating bacteria and the organic matter in the treating liquid on the carrier, thereby effectively realizing the hydrogen production by the hydrogen-generating bacteria.

According to the method for manufacturing hydrogen of the present invention, hydrogen fermentation can be efficiently and stably conducted even if the treating liquid contains solid matter, and the flow out of the hydrogen-generating bacteria from the hydrogen fermentor can be fully suppressed.

The string-shape carrier used in the method for manufacturing hydrogen according to the present invention preferably has a braid structure in which fibers form a lace-like pattern. With that string-shape carrier having the braid structure, a large quantity of hydrogen-generating bacteria can be fixed on the string-shape carrier. In addition, the holdability of organic matter on the string-shape carrier and the separability of adhered substances and hydrogen gas from the string-shape carrier can be improved.

According to the method for manufacturing hydrogen of the present invention, it is preferable that the string-shape carrier is held by a holder in a stretching state by fixing both ends of the string-shape carrier. With the configuration, a desired positioning of the string-shape carrier is attained while fully assuring the holdability of the organic matter on the string-shape carrier, thus increasing the freedom of the apparatus design. In addition, when the hydrogen fermentation apparatus has a plurality of string-shape carriers, the interwinding phenomenon of the string-shape carriers with each other under a generated flow of treating liquid is prevented.

The holder preferably comprises two end faces which are positioned to face with each other and have a network structure, and the frame which holds the two end faces at a specified distance therebetween. With the configuration, the treating liquid passes through the mesh opening at the end face of the holder even when a flow of treating liquid occurred along the stretching direction of the string-shape carrier, thus the reduction of contact efficiency between the hydrogen-generating bacteria fixed on the string-shape carrier and the organic matter is fully suppressed.

In the method for manufacturing hydrogen according to the present invention, it is preferable that the mixing means having the stirrer which is capable of rotating around the rotary shaft extending in the stretching direction of the string-shape carrier is applied and the hydrogen fermentation is conducted under agitation of the treating liquid in the hydrogen fermentor by the mixing means. With that mixing means to agitate the treating liquid in the hydrogen fermentor, the flow of the treating liquid reaches deep into the fibers of the string-shape carrier, which further improves both the holdability of organic matter on the fixing carrier and the separability of adhered substances and hydrogen gas from the fixing carrier, thus achieving extremely high level of treatment efficiency.

In the method for manufacturing hydrogen according to the present invention, it is preferable that the mixing means is applied, the mixing means having the circulation line connected to the hydrogen fermentor at both ends thereof and creating a flow of the treating liquid in the hydrogen fermentor by withdrawing the treating liquid in the hydrogen fermentor from one end thereof and introducing the treating liquid into the hydrogen fermentor from the other end thereof, and the hydrogen fermentation is conducted under mixing of the treating liquid in the hydrogen fermentor by the mixing means. With that circulation line to circulate the treating liquid in the hydrogen fermentor, extremely high level of treatment efficiency is attained. Further, for a mixing means that has the circulation line and that has no stirrer, there exists no influence of shearing force caused by the stirrer. Therefore, even when the hydrogen-generating bacteria which are likely affected by the shearing force during the growth period thereof are used, the hydrogen production by the hydrogen-generating bacteria is favorably realized.

Effect of the Invention

As described above, the hydrogen fermentation apparatus according to the present invention efficiently and stably treats the treating liquid on generating hydrogen from organic matter through the hydrogen fermentation even if the treating liquid contains solid matter, and fully suppresses the flow out of the hydrogen-generating bacteria from the hydrogen fermentor. Specifically, if the treating liquid contains a large quantity of solid matter, the above effects of the present invention are fully performed to generate sufficient quantity of hydrogen and to sufficiently decrease the quantity of solid matter in the treating liquid.

Furthermore, the method for manufacturing hydrogen according to the present invention sufficiently and stably holds the hydrogen-generating bacteria and the organic matter in the treating liquid by applying string-shape carrier as the carrier to fix the hydrogen-generating bacteria, thus effectively realizes the solubilization of organic solid matter and the generation of hydrogen by the hydrogen-generating bacteria.

DESCRIPTION OF THE REFERENCE SYMBOLS

Figure 1:
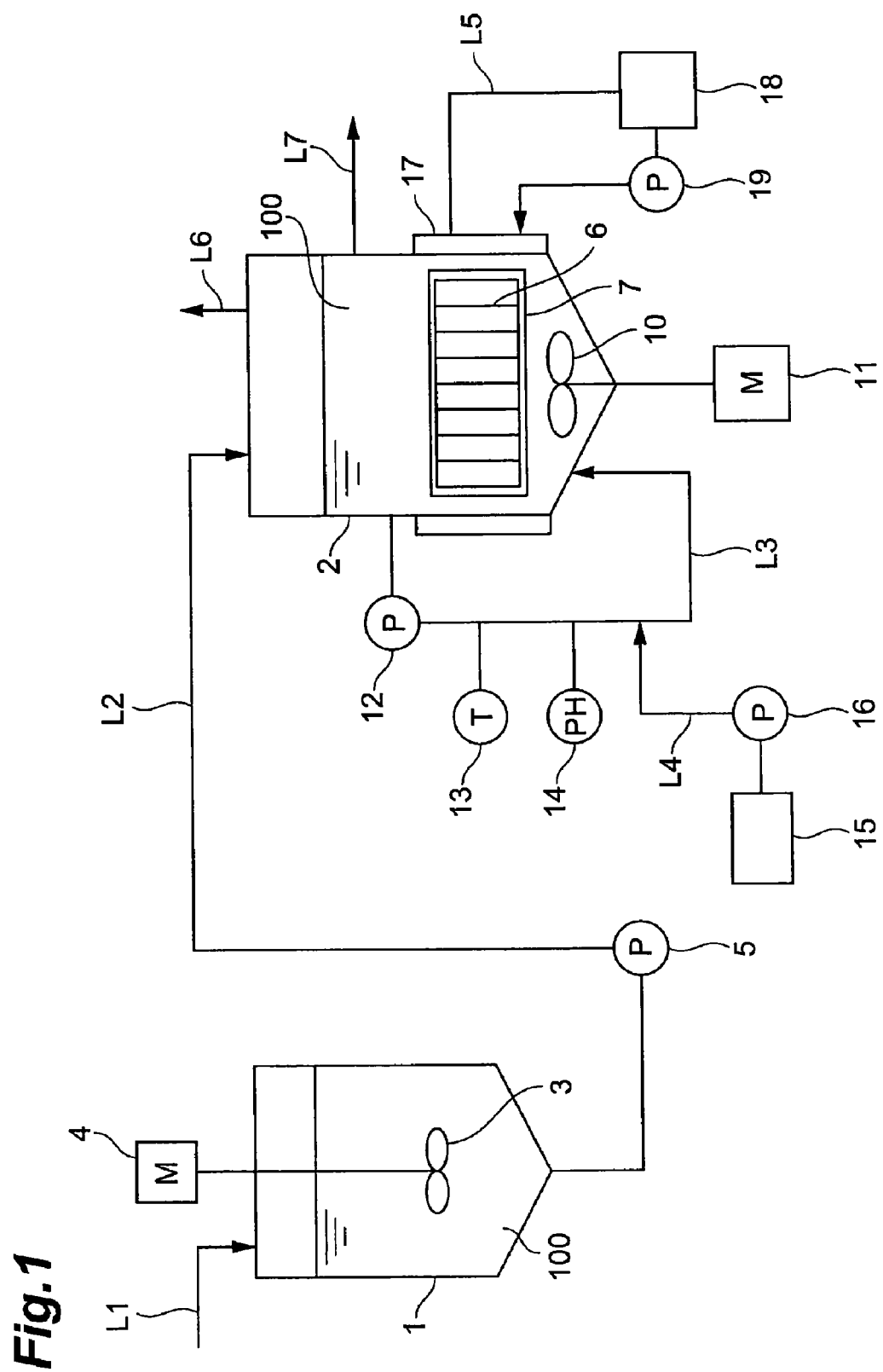
FIG. 1 is a block diagram of a first embodiment suitable for a hydrogen fermentation apparatus according to the present invention.

1: Raw material tank
2: Hydrogen fermentor
3, 10: Stirrer
4, 11: Motor
5, 12, 16, 19: Pump
6: String-shape carrier
7: Holder
8a, 8b: End face
9: Frame
13: Thermometer
14: pH meter
15: Alkali feeder
17: Tank jacket
18: Temperature controller
100: Treating liquid
L3, L8: Circulation line

BEST MODE FOR CARRYING OUT THE INVENTION

The preferred embodiments of the present invention are described in detail in the following referring to the drawings. The same element has the same reference symbol for all the drawings, and duplicated description is omitted. For convenience of referring to the drawings, the dimensional ratios of the drawings do not necessarily agree with those given in the description.

FIG. 1 is a block diagram of the first embodiment suitable for the hydrogen fermentation apparatus according to the present invention. As shown in FIG. 1, the hydrogen fermentation apparatus according to the first embodiment contains a raw material tank 1 and a hydrogen fermentor 2. As described later, the hydrogen fermentor 2 contains a string-shape carrier 6 on which hydrogen-generating bacteria are fixed so as to be immersed in treating liquid 100.

The raw material tank 1 connects a introduction line L1 which introduces the treating liquid 100 containing organic matter as the raw material liquid into the tank. The raw material tank 1 has an agitator which is structured by a stirrer 3 and a motor 4. With the agitator, the treating liquid 100 held in the raw material tank 1 is agitated before charged from the raw material tank 1 to the hydrogen fermentor 2, thus uniformly dispersing the solid matter into the liquid.

The treating liquid 100 is not specifically limited if only it contains organic matter which can be treated by hydrogen fermentation by the hydrogen-generating bacteria. Examples of the treating liquid 100 are food residue and organic waste liquids such as wastewater discharged from houses, restaurants, food plants, and the like. The first embodiment is useful in treating biomass such as organic waste and organic wastewater among those organic waste liquids, aiming to obtain energy gas from reproducible organic resources, and in particular it is preferably applied to the treatment of brewery effluent, waste of bread-making, waste of sugar-making (sugar cane waste), waste of starch-making (cassaya waste), and the like.

The raw material tank 1 is connected to the hydrogen fermentor 2 via a transfer line L2. The transfer line L2 is equipped with a transfer pump 5 which supplies the treating liquid 100 from the raw material tank 1 to the hydrogen fermentor 2. Instead of the transfer pump 5, the difference of water level between the raw material tank 1 and the hydrogen fermentor 2 may be utilized to charge the treating liquid 100 from the raw material tank 1 to the hydrogen fermentor 2.

In the hydrogen fermentor 2, the hydrogen-generating bacteria are fixed on plurality units of string-shape carrier 6, which are fixed to the holder 7 at both ends thereof, thus arranging the string-shape carriers stretched in the depth direction of the treating liquid 100.

Figure 2:
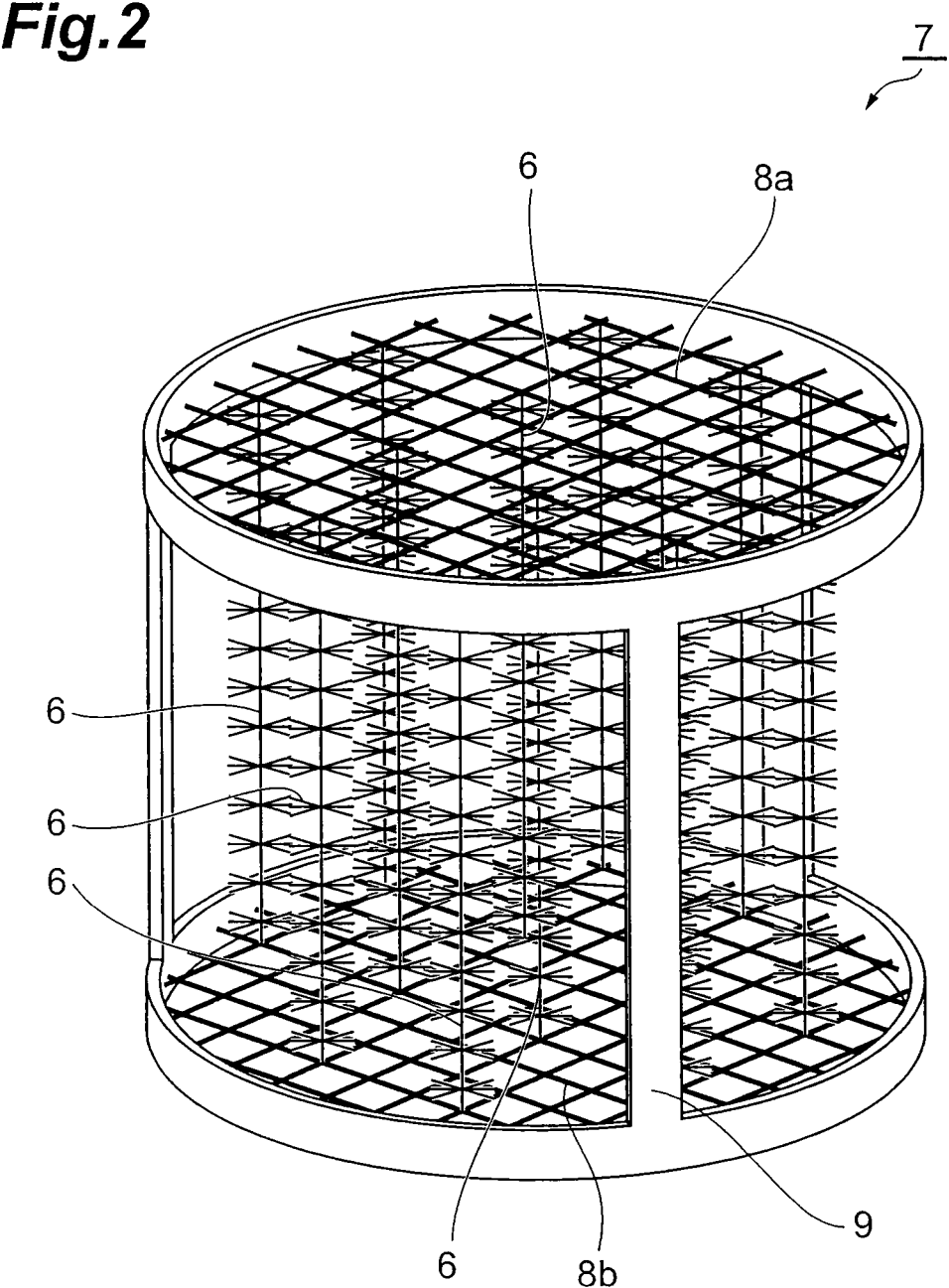
FIG. 2 is a perspective view of an example of string-shape carrier and of holder used in the present invention.

Although the string-shape carrier 6 is not specifically limited if only it can fix the hydrogen-generating bacteria thereon, it is preferably the one having flexibility. Specifically preferable one is, as shown in FIG. 2, the one having a braid structure which formed a plurality of small loops of fibers in the lace-like pattern. That type of string-shape carrier 6 having the braid structure can be formed by a core string-body structured by a fibrous material made of a synthetic resin and by a plurality of loop fibrous materials or string body extending radially from the core string body. With the use of that string-shape carrier 6 having the braid structure, the hydrogen-generating bacteria can be fixed to the string-shape carrier 6 in a large quantity, and further there is improved the holdability of organic matter on the string-shape carrier 6 and the separability of excess adhered substances and hydrogen gas from the string-shape carrier 6. When the string-shape carrier 6 has the braid structure, the string-shape carrier 6 preferably has rigidity to a degree that does not induce the collapse of lace-like pattern fibers to lose the void therein. Preferable fibers to form the string-shape carrier 6 are resins having durability, and specifically preferred ones are the fibers of polypropylene, polyamide (nylon), polyvinylalcohol (vinylon), polyvinylidene chloride, and a combination of two or more of them.

The specific surface area of the string-shape carrier 6 per unit length is preferably in a range from 0.3 to 4.0 $m^2/m$, and more preferably from 1.0 to 3.0 $m^2/m$.

The length of the string-shape carrier 6 may be adequately selected depending on the size of the hydrogen fermentor 2 and on the throughput of the treating liquid 100. It is, however, preferred to have a length that allows the total of the string-shape carrier 6 in a stretched state to immerse in the treating liquid 100, in view of the treatment efficiency. For example, as shown in FIG. 1, when the string-shape carrier 6 is positioned so as to stretch in the depth direction of the treating liquid 100, the length of the string-shape carrier 6 is preferably shorter than the depth of the treating liquid 100.

The number of string-shape carriers 6 is not specifically limited, and it may be adequately selected depending on the size of the hydrogen fermentor 2 and the thickness of the string-shape carrier 6. When the hydrogen fermentor 2 is provided with plurality units of string-shape carrier 6, it is preferable that the units of string-shape carrier 6 are arranged at a distance from each other so as the treating liquid 100 to be allowed passing between the string-shape carriers 6 in the stretching direction. When the inner capacity of the hydrogen fermentor 2 is small compared with the size of the string-shape carrier 6, the string-shape carriers 6 may be positioned in a spiral form along the inner periphery of the hydrogen fermentor 2, instead of fixing the string-shape carrier 6 on the holder 7 in a stretched state. Spiral arrangement of the string-shape carrier 6 is preferable because further long string-shape carrier 6 can be held in the hydrogen fermentor 2.

As shown in FIG. 2, the holder 7 is structured by two end faces 8a and 8b, being positioned to face with each other and having a network structure, and a frame 9 which holds the end faces 8a and 8b at a specified distance therebetween. Each string-shape carrier 6 is fixed to the end faces 8a and 8b at the respective ends thereof, thus being held in a stretched state thereof. By holding the string-shaped carrier 6 by that holder 7 in a stretched state thereof, there can be conducted efficiently and surely the contact between the organic matter in the treating liquid 100 and the hydrogen-generating bacteria fixed on the string-shape carrier 6, the separation of unnecessary solid matter, dead hydrogen-generating bacteria, and the like adhered to the surface of the string-shape carrier 6, and further the separation of hydrogen gas generated deep in the fibers of string-shape carrier 6, under any flow direction of the treating liquid 100 in the hydrogen fermentor 2. For example, when a flow of the treating liquid occurs along the stretching direction of the string-shape carrier 6, the above effects are effectively attained because the treating liquid 100 passes through the mesh opening of end face 8a or 8b of the holder 7.

The hydrogen-generating bacteria fixed on the string-shape carrier 6 are not specifically limited if only they have a hydrogen-generating ability. Applicable hydrogen-generating bacteria include: anaerobic microorganisms such as *Clostridia, Thermoanaerobacteriales, Methylotrophs, RumenBacteria*, and *Archaebacteria*; facultative anaerobic microorganisms such as *Esherihia coli and Enterobacter*; aerobic microorganisms such as *Alcaligenes* and *Bacillus*; photosynthetic bacteria; and *Cyanobacteria*. The hydrogen-generating bacteria may be prepared from isolated microorganisms or from mixed microorganisms communities (microflora) suitable for hydrogen production. When the hydrogen fermentation is conducted using these hydrogen-generating bacteria, there are generated fermentation gas (biogas) consisting mainly of hydrogen ($H_2$) and carbon dioxide ($CO_2$), and organic acids such as acetic acid, butyric acid, and lactic acid. For example, by the action of hydrogen-generating bacteria, glucose is decomposed into acetic acid ($CH_3COOH$), hydrogen, and carbon dioxide following the formula (1).

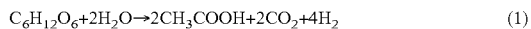

$$C_6H_{12}O_6 + 2H_2O \rightarrow 2CH_3COOH + 2CO_2 + 4H_2 \quad (1)$$

The hydrogen-generating bacteria are preferably fixed on the string-shape carrier 6 before the introduction of the treating liquid 100 to the hydrogen fermentor 2. However, the hydrogen-generating bacteria may be introduced to the hydrogen fermentor 2 together with a specified quantity of the treating liquid 100, and then fixed on the string-shape carrier 6. If the hydrogen-generating bacteria are introduced to the hydrogen fermentor 2 together with the treating liquid 100, it is preferable that the continuous fermentation begins after a running-in operation of the apparatus to enter a stable state of the hydrogen fermentation.

Referring again to FIG. 1, the hydrogen fermentor 2 has the agitator composed of a stirrer 10 which is positioned so as the rotary shaft to become nearly parallel to the stretching direction of the string-shape carrier 6, and a motor 11 to drive the stirrer 10. With that agitator to agitate the treating liquid 100 in the hydrogen fermentor 2, the flow of treating liquid 100 reaches deep into the fibers of the string-shape carrier 6, which further improves both the holdability of organic matter on the fixing carrier and the separability of adhered substances and hydrogen gas from the string-shape carrier 6, thus achieving extremely high level of treatment efficiency.

The hydrogen fermentor 2 has a circulation line L3 which has a pump 12, a thermometer 13, and a pH meter 14. Further, the circulation line L3 is connected to an alkali feeder 15 at downstream side of the pH meter 14 via a line L4 having a pump 16. The alkali feeder 15 adds the alkali aqueous solution (NaOH aqueous solution, for example) to the treating liquid 100 in case of decreasing in the pH of the treating liquid 100 caused by the generation of acid during the progress of hydrogen fermentation. The hydrogen fermentor 2 has a tank jacket 17 at outer peripheral surface thereof. The tank jacket 17 is connected to a circulation line L5 which circulates and supplies the heating medium (warm water, for example), controlled to a specified temperature by a temperature controller 18, to the tank jacket 17 by a pump 19. The thermometer 13, the temperature controller 18, the pH meter 14, and the alkali feeder 15 are linked with each other to control the temperature and the pH of the treating liquid 100 in the hydrogen fermentor 2 based on the temperature and the pH of the treating liquid 100 which is withdrawn by the pump 12 into the circulation line L3. A preferable treatment condition of the hydrogen fermentation using anaerobic microorganisms communities is about 5.0 to about 7.5 of pH and about 20° C. to about 70° C. of temperature.

The hydrogen fermentation apparatus according to the first embodiment has, as shown in FIG. 1, the withdrawal opening (discharge opening) for the circulation line L3 from the hydrogen fermentor 2 positioned above the recycle opening (introduction opening) to the hydrogen fermentor 2. With that configuration, upward flow (further convection) of the treating liquid 100 in the hydrogen fermentor 2 occurs, which suppresses the sedimentation of solid matter in the treating liquid 100 to the bottom of the hydrogen fermentor 2. As a result, there are attained further improvement both in the holdability of organic matter in the treating liquid 100 on the string-shape carrier 6 and in the separability of adhered substances (unnecessary solid matter, dead hydrogen-generating bacteria, and the like) and hydrogen gas from the string-shape carrier 6.

Use of the string-shape carrier 6 as the fixing carrier of the hydrogen-generating bacteria allows sufficient and stable holding of the organic matter in the treating liquid 100 on the carrier, and realizes effective execution of the hydrogen fermentation by hydrogen-generating bacteria. Since the string-shape bacteria 6 is flexible, there are attained efficient and sure separation of unnecessary solid matter, dead hydrogen-generating bacteria, and the like adhered to the surface of the string-shape carrier 6, and separation of hydrogen gas generated deep in the fibers of the string-shape carrier 6 owing to the introduction or discharge of the treating liquid 100 to and from the hydrogen fermentor 2, the agitation by the agitator, and the flow of treating liquid 100 induced by the circulation through the circulation line L3, and the like. Furthermore, since the hydrogen-generating bacteria are fixed on the string-shape carrier 6, there is no need of separation means to separate the carrier from the treating liquid 100, as required in the conventional fluidized bed method, and further the flow out of the hydrogen-generating bacteria from the hydrogen fermentor 2 is fully suppressed. Consequently, even if the treating liquid 100 contains solid matter, there is available a hydrogen fermentation apparatus which conducts the hydrogen fermentation efficiently and stably, and which fully suppresses the flow out of the hydrogen-generating bacteria from the hydrogen fermentor 2.

When the treating liquid 100 contains a large quantity of solid matter, the above effects are maximized, and a plenty volume of hydrogen can be generated while fully decreasing the quantity of solid matter in the treating liquid 100.

The hydrogen gas generated by the hydrogen fermentation is collected through a gas collection line L6 located at top of the hydrogen fermentor 2. On the other hand, the treating liquid 100 after the hydrogen fermentation, (the fermented liquid), is discharged from the fermentor via a discharge line L7. Although the connecting position of the discharge line L7 with the hydrogen fermentor 2 is not specifically limited, above the upper end of the string-shape carrier 6 can suppress the inclusion of solid matter into the fermented liquid. The discharge method of the fermented liquid is not specifically limited, and any of overflow type and pump forceful discharge may be applied.

Although the string-shape carrier 6 sustains the performance over a long period of time, if the performance deterioration of the string-shape carrier 6 is observed, the string-shape carrier 6 can be replaced by detaching a top cover to open the hydrogen fermentor 2, then by taking out the string-shape carrier 6 from the hydrogen fermentor 2.

Figure 3:
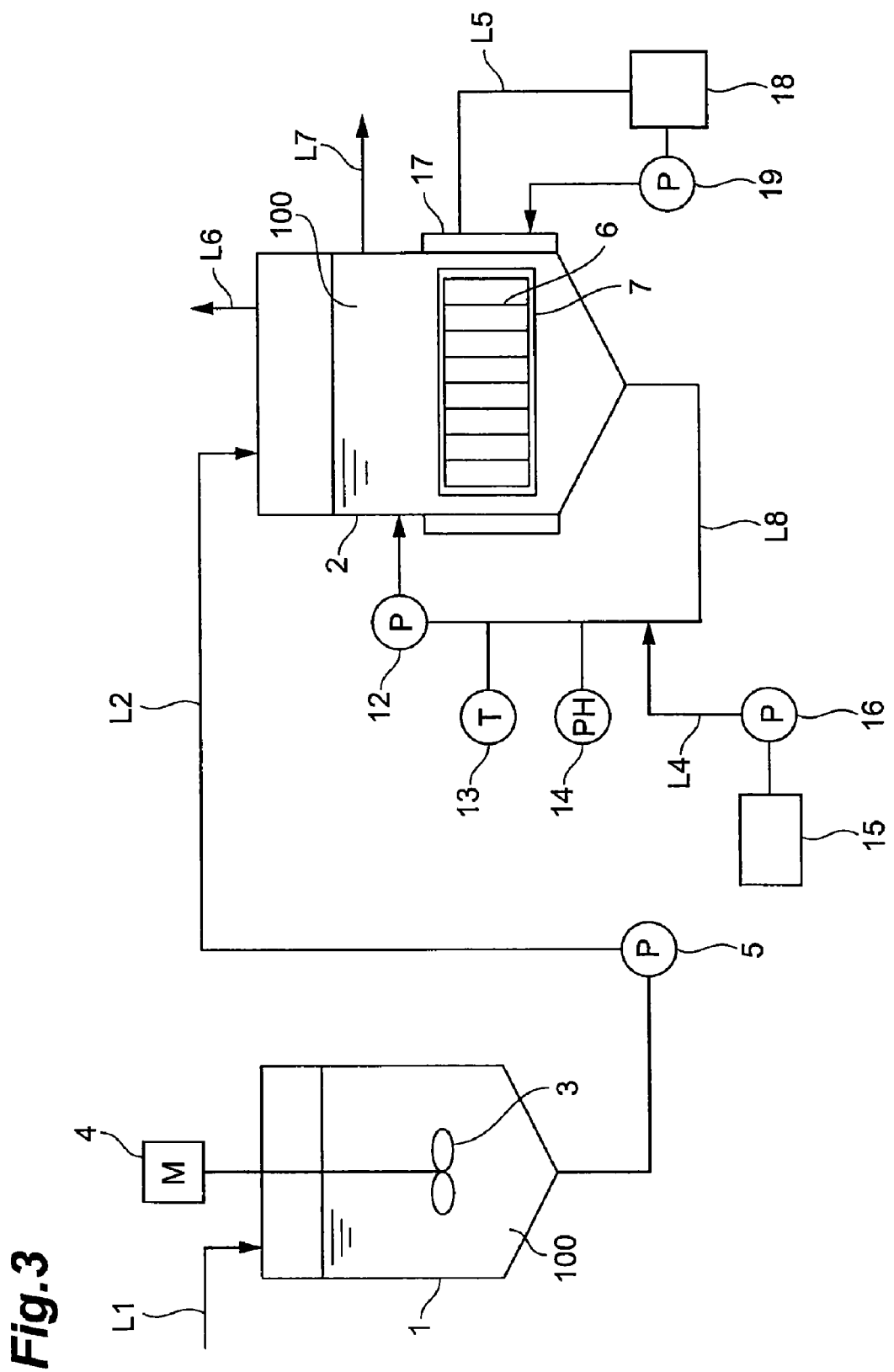
FIG. 3 is a block diagram of a second embodiment suitable for the hydrogen fermentation apparatus according to the present invention.

FIG. 3 is a block diagram of the second embodiment suitable for the hydrogen fermentation apparatus according to the present invention. Similar to the first embodiment, the hydrogen fermentation apparatus of the second embodiment is structured by containing the raw material tank 1 and the hydrogen fermentor 2. The hydrogen fermentor 2 contains the string-shape carrier 6 on which the hydrogen-generating bacteria are fixed so as to be immersed in the treating liquid 100. A circulation line L8 is provided as the mixing means, which is described below.

The circulation line L8 is connected to the bottom of the hydrogen fermentor 2 at one end thereof, and to the side of the hydrogen fermentor 2 at the other end thereof. The connection part of the bottom of the hydrogen fermentor 2 with the circulation line L8 is the withdrawal opening of the treating liquid 100, and the connection part of the side of the hydrogen fermentor 2 with the circulation line L8 is the recycle opening of the treating liquid 100 to the hydrogen fermentor 2. That is, the treating liquid 100 in the hydrogen fermentor 2 is withdrawn from the withdrawal opening to the circulation line L8, and the treating liquid 100 is introduced to the hydrogen fermentor 2 from the recycle opening, thus creating the flow of treating liquid 100 in the hydrogen fermentor 2 to mix the treating liquid 100 in the hydrogen fermentor 2.

The connection portion of the circulation line L8 with the hydrogen fermentor 2 is requested only to circulate the treating liquid 100 in the hydrogen fermentor 2 by the circulation line L8 and to cause the flow of treating liquid 100 to reach deep into the fibers of the string-shape carrier 6 without using the stirrer 10.

A preferable positioning of the withdrawal opening and the recycle opening is, for example, the connection of the hydrogen fermentor 2 with the circulation line L8 so as the withdrawal opening to come above the top of the holder 7, and so as the recycle opening to come below the bottom of the holder 7. With the configuration, the flow of treating liquid 100 along the stretching direction of the string-shape carrier 6 in the hydrogen fermentor 2 is created, thus the contact efficiency between the string-shape carriers 6 and the treating liquid 100 is improved.

Further, when the withdrawal opening is positioned below the bottom of the holder 7 and when the recycle opening is positioned above the top of the holder 7, the following advantages are acquired. That configuration is suitable for, for example, the case that the treating liquid 100 contains a large quantity of solid matter. That is, even if the solid matter in the treating liquid 100 sediments to the bottom of the hydrogen fermentor 2, the sedimented solid matter is withdrawn together with the treating liquid 100 from the withdrawal opening into the circulation line L8, and then returned to the hydrogen fermentor 2 from the recycle opening provided above the top of the holder 7, thus the effective quantity of the solid matter being able to contact with the string-shape carrier 6 is maintained at a high level. If the withdrawal opening is positioned above the top of the holder 7, and if the recycle opening is positioned below the bottom of the holder 7, it is necessary to blow up the sedimented solid matter using the treating liquid 100 coming from the recycle opening to cause the sedimented solid matter to suspend in the treating liquid 100, which needs to increase the circulation flow velocity. To the contrary, if the withdrawal opening is positioned below the bottom of the holder 7, and if the recycle opening is positioned above the top of the holder 7, similar effect is attained with a relatively low circulation flow velocity.

For the case of the second embodiment in which no agitator is applied and only the circulation line L8 is adopted to perform the mixing of treating liquid 100, convection is generated in the hydrogen fermentor 2 along the line between the withdrawal opening and the recycle opening of the circulation line L8. Accordingly, it is preferable to position the string-shape carrier 6 in almost horizontal position in view of reaching the flow of treating liquid deep into the fibers of the string-shape carrier.

The present invention is not limited to the first embodiment and the second embodiment. For example, even if the mixing means to mix the treating liquid 100 in the hydrogen fermentor 2 has only the agitator (stirrer 10 and motor 11) given in the first embodiment and does not have the circulation lines L3 and L8, it is satisfactory if the stirrer 10 achieves agitation to cause the flow of treating liquid 100 to reach the fibers of the string-shape carrier 6. In that case, the positioning of the string-shape carrier 6 is preferably similar to that of the first embodiment.

The first embodiment and the second embodiment showed examples of fixing both end of the string-shape carrier 6 to the holder 7. If the string-shaped carrier 6 can be kept in a stretched state in the treating liquid 100, and if the interwinding of string-shape carriers 6 with each other can be prevented, the fixation of the string-shape carrier 6 may be given only one end thereof. Furthermore, as the means to control the temperature of treating liquid 100 in the hydrogen fermentor 2, coil, heat exchanger, and the like may be applied instead of the tank jacket 17, and further the temperature control may be done by mixing a heating medium such as warm water with the treating liquid 100.

EXAMPLES

The present invention is described below in more detail referring to Examples and Comparative Examples. However, the present invention is not limited in any means to the following Examples.

Example 1

First, there were prepared 100 units of string-shaped carrier (0.3 m in length and 1.02 $m^2/m$ of specific area per unit length) having a braid structure which formed a plurality of small loops of fibers (nylon+polypropylene) in the lace-like pattern. Both ends of the string-shape carrier were fixed on a holder made of stainless steel (SUS) having the structure given in FIG. 2. The string-shape carrier being held on the holder in a stretched state was positioned in the hydrogen fermentor (900 L of capacity) of the hydrogen fermentation apparatus shown in FIG. 1 so as the stretching direction of the string-shape carrier to become vertical direction. In Example 1, the hydrogen-generating microorganisms communities containing closely related species of the hydrogen-generating bacteria, *Thermoanaeorobacterium thermoshaccharolyticum*, were propagated in advance in a seed bacteria culture tank, which were then applied to the hydrogen fermentation treatment.

Then, to the raw material tank of the hydrogen fermentation apparatus, water and bread waste were charged to prepare the raw material liquid. The concentration of the bread waste in the raw material liquid was adjusted to 33 kg of the bread waste per 1 $m^3$ of the raw material liquid. A 490 L aliquot of thus prepared raw material liquid and 10 L aliquot of above hydrogen-generating microorganisms communities were charged to the hydrogen fermentor of the hydrogen fermentation apparatus, which were then subjected to propagation of hydrogen-generating bacteria and to fix to the string-shape carrier at 50° C. for 72 hours under agitation. After that, the raw material liquid was continuously charged to the hydrogen fermentor at a rate of 250 L/day. The quantity of the liquid in the fermentor was 500 L, and the retention time of the fermented liquid was 48 hours. The temperature of the fermented liquid was controlled to 50° C. and the pH was controlled to 6. The agitator was operated at 80 rpm. The fermented liquid at a specified retention time in the fermentor under agitation was continuously discharged from the fermentor via the discharge opening as the treated liquid.

Figure 4:
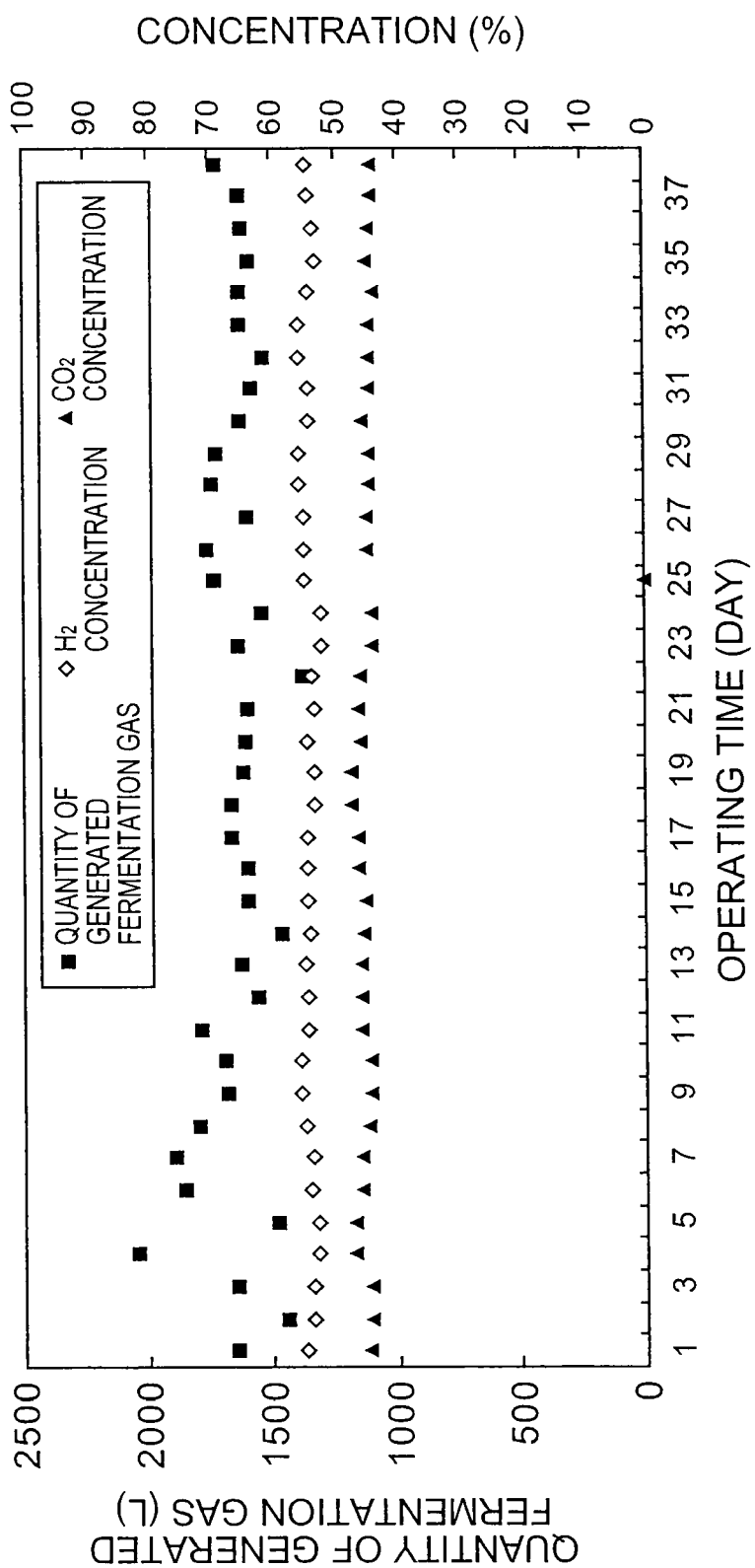
FIG. 4 is a graph showing the relation between the quantity of generated fermentation gas and the operating time in the hydrogen fermentation test of Example 1.

FIG. 4 shows the relation between the quantity of generated fermentation gas and the operating time in the above hydrogen fermentation test. The quantity of generated fermentation gas was stable to the quantity of charged treating liquid throughout the test. The hydrogen concentration in the fermentation gas was about 55%, and the generation of carbon dioxide as the second component was confirmed.

Figure 5:
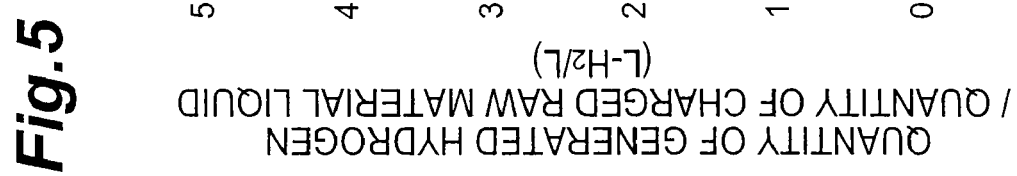
FIG. 5 is a graph showing the relation between the quantity of generated hydrogen to the quantity of charged raw material liquid and the operating time in the hydrogen fermentation test of Example 1.

FIG. 5 shows the relation between the ratio of the quantity of generated hydrogen to the quantity of charged raw material liquid and the operating time in the above hydrogen fermentation test. In the test, 3 to 4 L of hydrogen was generated to 1 L of charged raw material liquid, and the ratio was stable throughout the test.

The results measured the weight of the solid matter (not smaller than SS size) in the treating liquid (raw material liquid) before introduced to the hydrogen fermentor 2 and in the treating liquid (fermentation waste liquid) discharged from the hydrogen fermentor 2 after a specified period of time after beginning the test are given in Table 1. As shown in Table 1, the test decreased the quantity of solid matter in the treating liquid by 74% as the average weight ratio.

TABLE 1

| CONCENTRATION OF SOLID MATTER IN RAW MATERIAL LIQUID | CONCENTRATION OF SOLID MATTER IN FERMENTATION WASTE LIQUID |
|---|---|
| $1^{ST}$ MEASUREMENT 16100 mg/L | $1^{ST}$ MEASUREMENT 5270 mg/L |
| $2^{ND}$ MEASUREMENT 19400 mg/L | $2^{ND}$ MEASUREMENT 4830 mg/L |
| $3^{RD}$ MEASUREMENT 18850 mg/L | $3^{RD}$ MEASUREMENT 4470 mg/L |
| $4^{TH}$ MEASUREMENT 17550 mg/L | $4^{TH}$ MEASUREMENT 4830 mg/L |
| $5^{TH}$ MEASUREMENT 15850 mg/L | $5^{TH}$ MEASUREMENT 4130 mg/L |
| $6^{TH}$ MEASUREMENT 17350 mg/L | $6^{TH}$ MEASUREMENT 4670 mg/L |
| $7^{TH}$ MEASUREMENT 21150 mg/L | $7^{TH}$ MEASUREMENT 4530 mg/L |
| $8^{TH}$ MEASUREMENT 17000 mg/L | $8^{TH}$ MEASUREMENT 4370 mg/L |
| $9^{TH}$ MEASUREMENT 16450 mg/L | $9^{TH}$ MEASUREMENT 4470 mg/L |
| $10^{TH}$ MEASUREMENT 19300 mg/L | $10^{TH}$ MEASUREMENT 4230 mg/L |
| AVERAGE 17900 mg/L | AVERAGE 4580 mg/L |

Example 2

There were prepared 40 units of string-shape carrier (0.5 m in length and 1.02 $m^2$/m of specific area per unit length) having a braid structure which formed a plurality of small loops of fibers (nylon+polypropylene) in the lace-like pattern. Each 20 units of them were fixed at both ends thereof to each one of the two holders made of stainless steel (SUS) having the structure shown in FIG. 2. The string-shape carrier which was thus held on the holder in a stretched state was placed in the hydrogen fermentor (220 L of capacity) of the hydrogen fermentation apparatus given in FIG. 3 so as the stretching direction of the string-shape carrier to become vertical direction. In Example 2, hydrogen-generating microorganisms communities containing closely related species of hydrogen-generating bacteria, *Thermoanaerobacterium thermosaccharolyticum*, were propagated in a seed bacteria culture tank in advance, which were then used for the hydrogen fermentation treatment.

A 200 L aliquot of the hydrogen-generating microorganisms communities was charged to the hydrogen fermentation apparatus, followed by charging continuously the raw material liquid to the hydrogen fermentor at a rate of 100 L/day. The quantity of liquid in the fermentor was 200 L, and the retention time of the fermentation liquid was 48 hours. The charged raw material liquid was bread waste diluted by water. The bread waste concentration was 25 kg/$m^3$ for 15 days of period until the string-shape carrier held sufficient quantity of microorganisms communities, and was 33 kg/$m^3$ after that. The fermentation liquid was adjusted to 60° C. and pH 6. By using the circulation line L8, the circulation (downward circulation) was established in the hydrogen fermentor at a flow rate of 3000 L/h, and the fermentation liquid after a specified retention time was continuously discharged from the fermentor via the discharge opening as the treated liquid.

Figure 6:
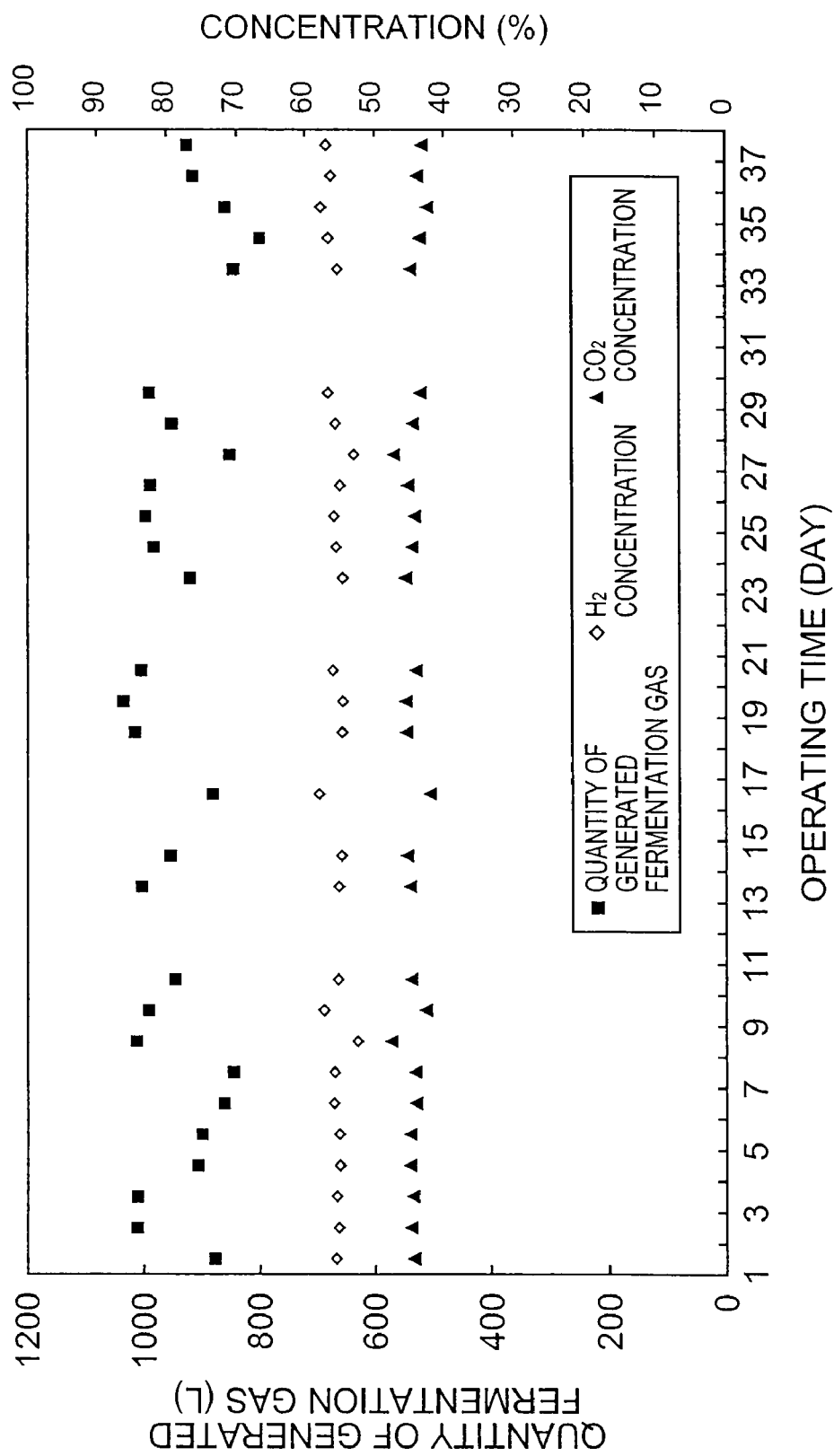
FIG. 6 is a graph showing the relation between the quantity of generated fermentation gas and the operating time in the hydrogen fermentation test of Example 2.

FIG. 6 shows the relation between the quantity of generated fermentation gas and the operating time in above hydrogen fermentation test. The quantity of generated fermentation gas was stable throughout the test against the quantity of charged treating liquid. The hydrogen concentration in the fermentation gas was about 55%, and the generation of carbon dioxide as the second component was confirmed.

Figure 7:
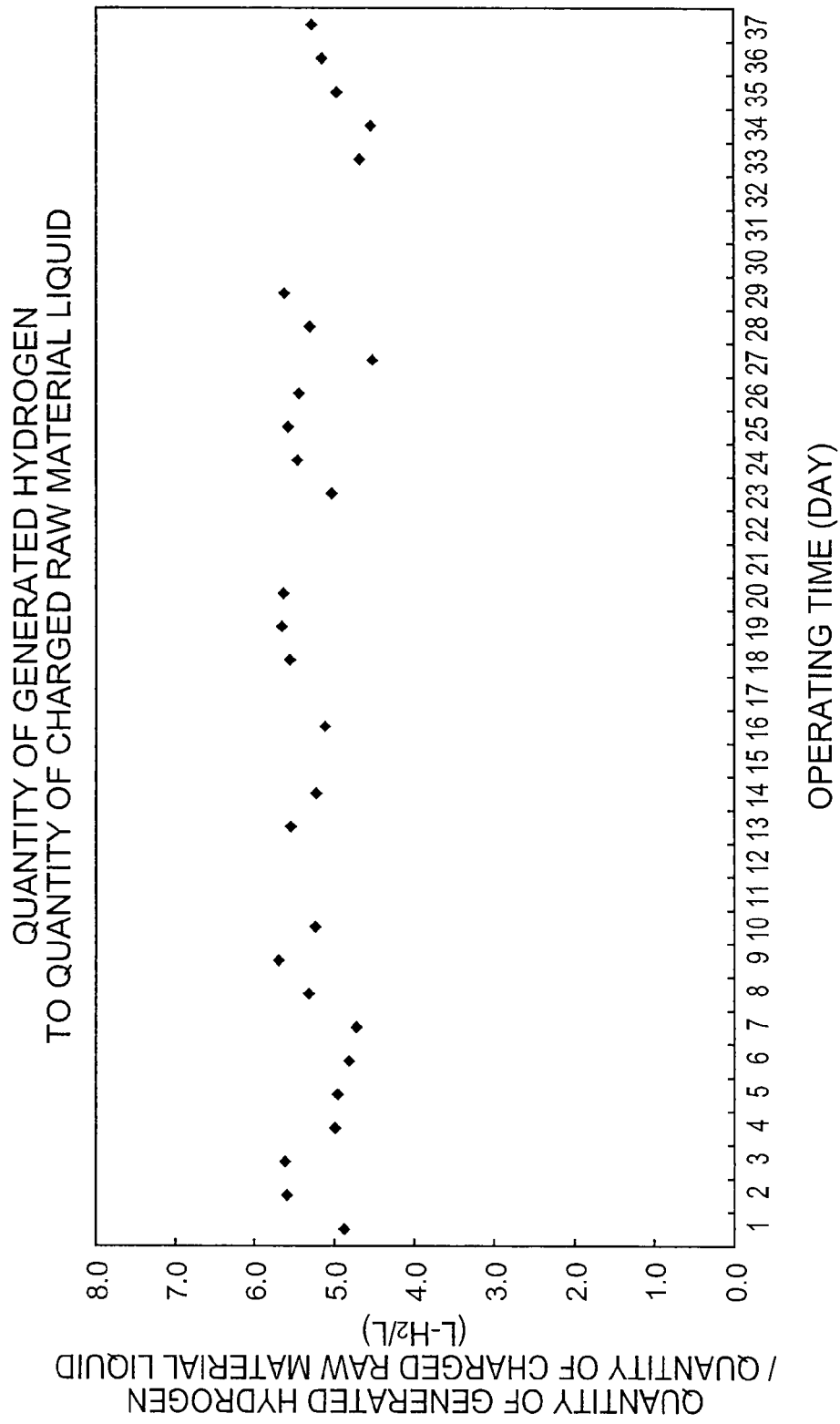
FIG. 7 is a graph showing the relation between the quantity of generated hydrogen to the quantity of charged raw material liquid and the operating time in the hydrogen fermentation test of Example 2.

FIG. 7 shows the relation between the ratio of the quantity of generated hydrogen to the quantity of charged raw material liquid and the operating time in the above hydrogen fermentation test. In the test, 4.5 to 5.5 L of hydrogen was generated to 1 L of charged raw material liquid, and the ratio was stable throughout the test.

Example 3

A single unit of string-shape carrier (0.25 m in length) similar to that of Example 1 was placed in a 1 L microorganisms culture apparatus (BMJ-01PI 1L, manufactured by ABLE Ltd.) in a spiral form along the inner peripheral surface of the apparatus. The apparatus was used as the hydrogen fermentor to conduct the following hydrogen fermentation test.

The inner space of the microorganisms culture apparatus containing the string-shape carrier was replaced by nitrogen gas. Then, 300 mL of hydrogen-generating microorganisms communities containing closely related species of hydrogen-generating bacteria, *Thermoanaerobacterium thermosaccharolyticum*, and 200 mL of brewery effluent were charged to the microorganisms culture apparatus to conduct hydrogen fermentation under the condition of 50° C., 6.0 to 6.5 of pH, and 125 rpm of agitation. The brewery effluent was prepared by sieving (200 mesh) the brewery effluent at Shizuoka Brewery of SAPPORO BREWERIES LTD. After sieving, the properties of the brewery effluent were pH 4, 15000 to 60000 mL of COD, 5000 to 16000 mg/L of total sugar (as glucose), 3000 to 4000 mg/L of maltose, 2500 to 9000 mg/L of lactic acid, and 100 to 300 mg/L of acetic acid.

After confirming the stable state of the hydrogen fermentation, 250 mL of culture medium (brewery effluent) was continuously charged, while continuously discharging the same quantity of culture solution to conduct the continuous culture. During the test, the quantity of generated hydrogen was maximum 611 mL per day, and the quantity of generated hydrogen to the charged quantity of medium (brewery effluent) was maximum 2.4 mL-$H_2$/mL.

Comparative Example 1

The inner space of a 2 L microorganisms culture apparatus (MBF, manufactured by TOKYO RIKAKIKAI CO., LTD.) was replaced by nitrogen gas. Then, 50 mL of hydrogen-generating microorganisms communities containing closely related species of hydrogen-generating bacteria, *Thermoanaerobacterium thermosaccharolyticum*, and 700 mL of brewery effluent similar to that of Example 3 were charged to the microorganisms culture apparatus to conduct hydrogen fermentation under the condition of 50° C., 6.0 to 6.5 of pH, and 125 rpm of agitation.

After confirming the stable state of the hydrogen fermentation, 2000 mL of culture medium (brewery effluent) was continuously charged, while continuously discharging the same quantity of culture solution to conduct the continuous culture. During the test, the quantity of generated hydrogen was maximum 2500 mL per day, and the quantity of generated hydrogen to the charged quantity of medium (brewery effluent) was maximum 1.25 mL-$H_2$/mL.

Comparative Example 2

The inner space of a 2 L microorganisms culture apparatus (MBF, manufactured by TOKYO RIKAKIKAI CO., LTD.) was replaced by nitrogen gas. Then, 600 mL (bulk volume) of sterilized diatom earth fired particle carrier (manufactured by SHOWA CHEMICAL INDUSTRY CO., LTD.), 100 mL of hydrogen-generating microorganisms communities containing closely related species of hydrogen-generating bacteria, *Thermoanaerobacterium thermosaccharolyticum*, and 900 mL of brewery effluent similar to that of Example 3 were charged to the microorganisms culture apparatus to conduct hydrogen fermentation under the condition of 50° C., 6.0 to 6.5 of pH, and 125 rpm of agitation.

After confirming the stable state of the hydrogen fermentation, the quantity of culture solution was decreased by 500 mL, and continuously charged 500 mL of culture medium (brewery effluent), while continuously discharging the same quantity of culture solution to conduct the continuous culture. During the test, the quantity of generated hydrogen was maximum 300 mL per day, and the quantity of generated hydrogen to the charged quantity of medium (brewery effluent) was maximum 0.6 mL-$H_2$/mL. After the test, there were found the sediments of large quantities of microorganisms and solid matter in the medium at bottom and peripheral area, which suggested that the gas generation was at a low level because of not active convection of the medium components.

Comparative Example 3

The inner space of a 5 L microorganisms culture apparatus (BMS-PI 5L, manufactured by ABLE Ltd.) was replaced by nitrogen gas. Then, 500 mL (bulk volume) of sterilized chitosan beads carrier (Chitopearl, manufactured by Fujibo Holdings, Inc.), 100 mL of acclimatized hydrogen-generating thermophilic bacterial communities, and 1900 mL of brewery effluent similar to that of Example 3 were charged to the microorganisms culture apparatus to conduct hydrogen fermentation under the condition of 50° C., 6.0 to 6.5 of pH, and 200 rpm of agitation.

After confirming the stable state of the hydrogen fermentation, 500 mL of culture medium (brewery effluent) was continuously charged, while continuously discharging the same quantity of culture solution to conduct the continuous culture. During the test, the quantity of generated hydrogen was maximum 100 mL per day, and the quantity of generated hydrogen to the charged quantity of medium (brewery effluent) was maximum 0.2 mL-$H_2$/mL. During the test, there was observed a phenomenon that, in the course of the progress of the holding of microorganisms on the chitosan beads carrier and of the increase of hydrogen gas generation, most of the carrier particles floated to the liquid surface, which suggested that the gas generation stayed at a low level owing to very few contacts with the medium components.

To compare the performance of hydrogen fermentation apparatus among Example 3 and Comparative Examples 1 to 3, Table 2 gives the dilution ratio, the ratio of the quantity of generated hydrogen to the quantity of charged raw material liquid, and the ratio of the quantity of generated hydrogen to the total reaction volume for the above tests. The term "dilution ratio" referred to herein signifies the inverse of average retention time of raw material liquid to the net liquid quantity in the fermentor, which is expressed by the formula (A):

$$D=F/V \qquad (A)$$

where, D is the dilution ratio (dimension of $T^{-1}$, (T is time)), F is the charged flow rate, and V is the net liquid quantity. The term "total reaction volume" referred to herein signifies the sum of the net liquid quantity in the fermentor and the volume of the fixing carrier.

TABLE 2

|  | EXAMPLE 3 | COMPARATIVE EXAMPLE 1 | COMPARATIVE EXAMPLE 2 | COMPARATIVE EXAMPLE 3 |
|---|---|---|---|---|
| DILUTION RATIO | 0.50 | 0.60 | 0.45 | 0.20 |
| QUANTITY OF GENERATED HYDROGEN/QUANTITY OF CHARGED RAW MATERIAL LIQUID (mL/mL) | 2.4 | 1.0 | 0.6 | 0.2 |
| QUANTITY OF GENERATED HYDROGEN/TOTAL REACTION VOLUME (mL/mL) | 1.22 | 0.6 | 0.27 | 0.04 |

Example 4

To grasp the influence of the string-shape carrier on the hydrogen fermentation, there were prepared string-shape carriers (0.2 m in length) having three kinds of braid structure, each having different material or different specific surface area. Each two units of the string-shape carrier were placed in a 30 L hydrogen fermentor of the hydrogen fermentation apparatus (HMF-30F01-30L culture tank, manufactured by Hitachi Ltd.) so as the stretching direction of the string-shape carrier to become vertical direction. The weight of cell bodies adhered to each string-shape carrier during the continuous fermentation was determined.

First, water and bread waste were charged to the raw material tank of above hydrogen fermentation apparatus to prepare the raw material liquid. The concentration of the bread waste in the raw material liquid was adjusted to 33 g of bread waste per 1 L of raw material liquid. A 14.5 L aliquot of thus prepared raw material liquid, and 0.5 L of hydrogen-generating microorganisms communities containing closely related species of hydrogen-generating bacteria, *Thermoanaerobacterium thermosaccharolyticum*, which were propagated in advance in a 1 L fermentor, were charged to a 30 L hydrogen fermentor, thus conducted propagation of hydrogen-generating bacteria and fixing operation of them on the string-shape carrier at 50° C. for 72 hours under agitation. After that, the raw material liquid was continuously charged to the hydrogen fermentor at a rate of 7.5 L/day. The quantity of the liquid in the fermentor was 15.0 L, and the retention time of the fermentation liquid was 48 hours. The fermentation liquid was adjusted to 50° C. and pH 6. The agitator was adjusted to 100 rpm. The fermentation liquid after a specified retention time in the fermentor under agitation was continuously discharged from the fermentor via the discharge opening as the treated liquid.

After continuous fermentation for 9 months, each string-shape carrier was taken out from the hydrogen fermentor, and the weight of cell bodies adhered to each string-shape carrier was determined. The weight of cell bodies in Table 3 means the weight of cell bodies adhered to each string-shape carrier per unit length.

TABLE 3

| MATERIAL OF STRING-SHAPE CARRIER | RATIO OF SURFACE AREA ($m^2/m$) | WEIGHT OF CELL BODIES (g/cm; WET) |
|---|---|---|
| POLYPROPYLENE | 3.00 | 9.2 |
| NYLON + POLYPROPYLENE | 0.35 | 2.4 |
| NYLON + POLYPROPYLENE | 1.02 | 4.4 |

Example 5

Into a 5 L microorganisms culture apparatus (BMS-05PI 5L, manufactured by ABLE Ltd.), 6 units of string-shape carrier (0.15 m in length) similar to that of Example 1 were placed so as the stretching direction of the strip-shape carrier to become vertical direction. The apparatus was used as the hydrogen fermentor to conduct the following hydrogen fermentation test.

First, a 500 g (wet weight) of cassaya waste (residue of starch production from cassaya) and 40 g of yeast extract were diluted by water to 5 L. The mixture was sterilized at 121° C. for 20 minutes to obtain the raw material liquid. Then, 0.5 L of hydrogen-generating microorganisms communities containing closely related species of hydrogen-generating bacteria, *Thermoanaerobacterium thermosaccharolyticum*, and 2 L aliquot of the raw material liquid were charged to the above hydrogen fermentor to conduct hydrogen fermentation under the condition of 55° C., 5.5 to 6.0 of pH, and 150 rpm of agitation.

After confirming the stable state of the hydrogen fermentation, about 0.3 to about 0.9 L of raw material liquid was continuously charged, while continuously discharging the same quantity of culture solution to conduct the continuous culture. During the test, the quantity of generated hydrogen was maximum 1.5 L per day, and the quantity of generated hydrogen to the charged quantity of cassaya waste was maximum 20 L-$H_2$/kg.

Example 6

Into a 5 L microorganisms culture apparatus (BMS-05PI 5L, manufactured by ABLE Ltd.), 6 units of string-shape carrier (0.15 m in length) similar to that of Example 1 were placed so as the stretching direction of the strip-shape carrier to become vertical direction. The apparatus was used as the hydrogen fermentor to conduct the following hydrogen fermentation test.

First, the inner space of a microorganisms culture apparatus containing the string-shape carrier was replaced by nitrogen gas. Then, 2.5 L of hydrogen-generating microorganisms communities containing closely related species of hydrogen-generating bacteria, *Thermoanaerobacterium thermosaccharolyticum*, was charged, and then a liquid of diluted bread waste was continuously charged while continuously discharging the equal quantity of culture solution to conduct the continuous culture. The culture condition was 55° C., 5.5 to 6.0 of pH, 150 rpm of agitation, 33 g/L of concentration of diluted bread waste liquid, and 0.5 L of the charge rate thereof per day. Under the above condition, after confirming the stable state of the hydrogen fermentation, the enzyme-treated cassaya waste was adopted as the raw material to conduct the hydrogen fermentation.

The procedure of enzyme treatment of cassaya waste is following. A 100 g (wet weight) of cassaya waste was homogenized, which was then diluted by ion-exchange water to 700 g. The mixture was adjusted to pH 4.0 using caustic soda. To the mixture, 0.1 g of SUMIZYME PMAC (manufactured by Shin Nihon Chemical Co., Ltd.) was added, thus conducted the enzyme treatment at 60° C. for 24 hours under shaking. Separately 6 g of yeast extract was dissolved in 50 mL of water, which was then sterilized at 121° C. for 20 minutes. Thus prepared sterilized yeast extract was added to the above enzyme-treated mixture to obtain the raw material liquid.

At every 24 hours, 0.7 L of raw material liquid was charged at a time, while continuously discharging the liquid at a constant rate of 0.7 L per day to conduct the continuous fermentation. The condition of fermentation was 55° C., 5.5 to 6.0 of pH, and 150 rpm of agitation (250 rpm only for 10 minutes immediately after charging the raw material liquid). During the test, the quantity of generated hydrogen was maximum 3.8 L per day, and the quantity of generated hydrogen to the charged quantity of cassaya waste was maximum 37 L-$H_2$/kg.

INDUSTRIAL APPLICABILITY

On generating hydrogen from organic matter through the hydrogen fermentation, the hydrogen fermentation apparatus according to the present invention efficiently and stably treats the treating liquid even when it contains solid matter, and fully suppresses the flow out of hydrogen-generating bacterial from the hydrogen fermentor. In particular, when the treating liquid contains a large quantity of solid matter, the above-described effects of the present invention are maximized to generate sufficient quantities of hydrogen, while fully decreasing the quantity of solid matter in the treating liquid.

The invention claimed is:

1. A method for manufacturing hydrogen by decomposing organic matter through hydrogen fermentation, comprising bringing a treating liquid comprising an organic matter into contact, within a hydrogen fermentor, with a string-shape carrier on which hydrogen-generating bacteria are fixed.

2. The method for manufacturing hydrogen according to claim 1, wherein the string-shape carrier has a braid structure in which fibers form a lace-like pattern.

3. The method for manufacturing hydrogen according to claim 1, wherein the string-shape carrier is held by a holder in a stretching state by fixing both ends of the string-shape carrier.

4. The method for manufacturing hydrogen according to claim 3, wherein the holder comprises two end faces which are positioned to face with each other and have a network structure, and the frame which holds the two end faces at a specified distance therebetween.

5. The method for manufacturing hydrogen according to claim 1, wherein a mixing means having a stirrer which is capable of rotating around a rotary shaft extending in the stretching direction of the string-shape carrier is applied and the hydrogen fermentation is conducted under mixing of the treating liquid in the hydrogen fermentor by the mixing means.

6. The method of manufacturing hydrogen according to claim 1, wherein a mixing means is applied, the mixing means having a circulation line connected to the hydrogen fermentor at both ends and creating a flow of the treating liquid in the hydrogen fermentor by withdrawing the treating liquid in the hydrogen fermentor from one end and introducing the treating liquid into the hydrogen fermentor from the other end, and the hydrogen fermentation is conducted under mixing of the treating liquid in the hydrogen fermentor by the mixing means.

7. The method for manufacturing hydrogen according to claim 1, wherein the hydrogen-generating bacteria is at least one selected from the group consisting of *Clostridia, Thermoanaerobacteriales, Methylotrophs RumenBacteria, Archaebacteria, Escherichia coli, Enterobacter, Alcaligenes, Bacillus,* and *Cyanobacteria*.

8. The method for manufacturing hydrogen according to claim 1, wherein the hydrogen-generating bacteria is *Thermoanaerobacterium thermosaccharolyticum*.

* * * * *